United States Patent [19]

Higham et al.

[11] Patent Number: 5,593,452
[45] Date of Patent: Jan. 14, 1997

[54] COATED FEMORAL STEM PROSTHESIS

[75] Inventors: Paul A. Higham, Ringwood, N.J.;
Larry T. Warfield, Hellertown, Pa.

[73] Assignee: Howmedica Inc., New York, N.Y.

[21] Appl. No.: 503,572

[22] Filed: Jul. 18, 1995

Related U.S. Application Data

[63] Continuation of Ser. No. 189,629, Feb. 1, 1994, abandoned.

[51] Int. Cl.⁶ .................................. A61F 2/32; A61F 2/28
[52] U.S. Cl. ................................ 623/23; 623/16; 606/76
[58] Field of Search .................................. 623/16, 18, 20,
623/22, 23, 66; 606/76

[56]  References Cited

U.S. PATENT DOCUMENTS

| | | | |
|---|---|---|---|
| 3,643,658 | 2/1972 | Steinemenan | 623/16 |
| 3,793,650 | 2/1974 | Ling et al. | 623/18 |
| 4,040,129 | 8/1977 | Steinemann et al. | 623/66 |
| 4,382,100 | 5/1983 | Holland | 427/38 |
| 4,394,400 | 7/1983 | Green et al. | 427/38 |
| 4,525,417 | 6/1985 | Dimigen et al. | 428/244 |
| 4,645,977 | 2/1987 | Kurokawa et al. | |
| 5,082,359 | 1/1992 | Kirkpatrick | 359/642 |
| 5,152,794 | 10/1992 | Davidson | 623/18 |
| 5,171,275 | 12/1992 | Ling et al. | 623/16 |

FOREIGN PATENT DOCUMENTS

| | | |
|---|---|---|
| 2178320A | 2/1987 | European Pat. Off. . |
| 0302717 | 2/1989 | European Pat. Off. . |
| 0573694A3 | 12/1993 | European Pat. Off. . |
| 1409054 | 10/1975 | United Kingdom . |

OTHER PUBLICATIONS

"Surface Modification of Medical Implants and Surgical Devices Using Tin Layers" by Bernard Coll & Patrick Jacquot, in Surface and Coatings Technology, vol. 36, 1988, pp. 867–878.

4 Multi-Arc brochures regarding coatings dating from 1987–1989.

*Primary Examiner*—David J. Isabella
*Attorney, Agent, or Firm*—Peter C. Richardson; Lawrence C. Akers; Raymond W. Augustin

[57]  ABSTRACT

A femoral hip component for use in hip arthroplasty has a stem portion for contact with bone cement. The stem portion is formed from a biocompatible material having a surface finish of less than about four microinches. This surface is coated with a uniform layer of material selected from the group consisting of diamond-like carbon, chromium carbide, titanium nitride, titanium carbo-nitride, chromium and zirconium and a combination thereof.

2 Claims, 3 Drawing Sheets

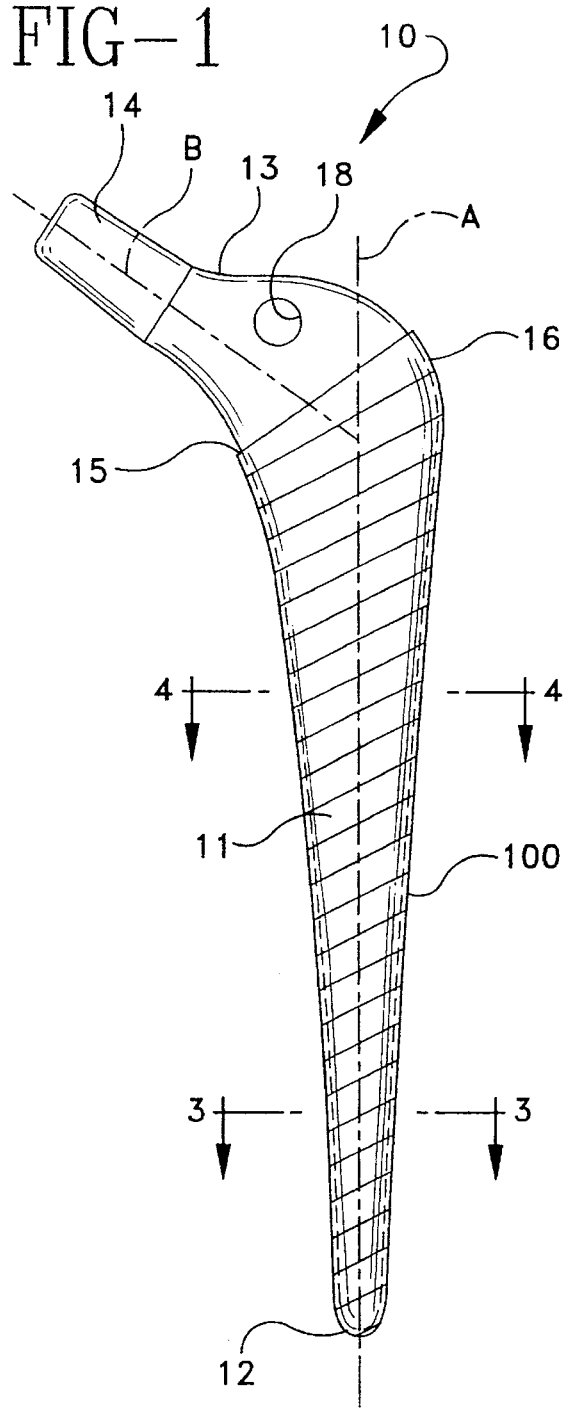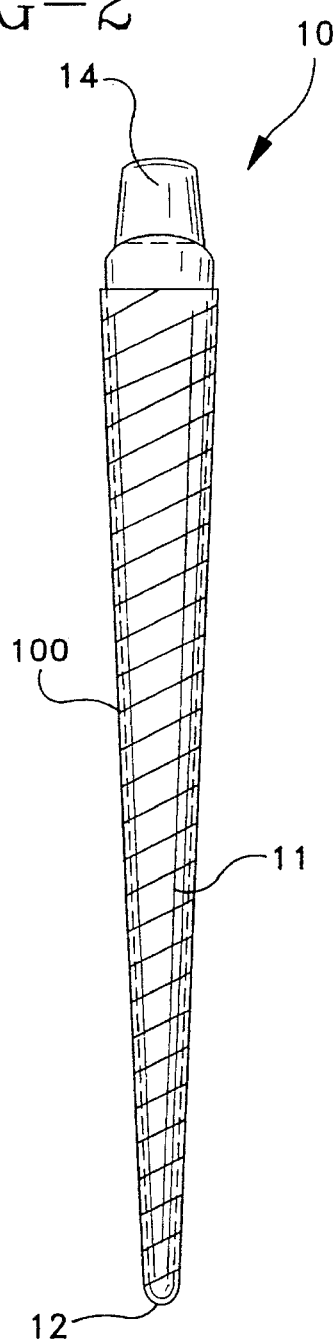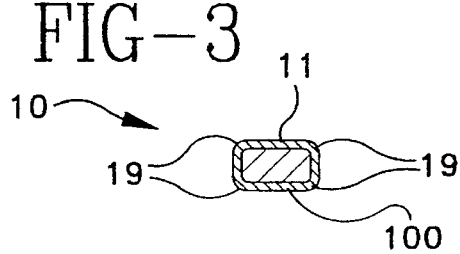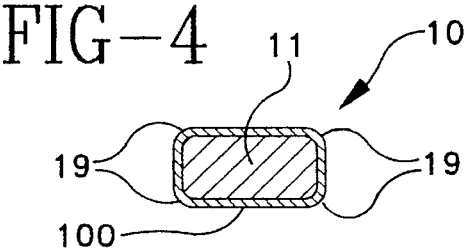

COATED FEMORAL STEM PROSTHESIS

This is a continuation of application Ser. No. 08/189,629, filed on Feb. 1, 1994 now abandoned.

BACKGROUND OF THE INVENTION

1. Field of the Invention

The present invention relates to a hip joint prosthesis and more particularly to a femoral component of such a prosthesis which is coated with a material which reduces the bonding of the prosthesis to bone cement,

2. Description of the Prior Art

Many methods and devices have been developed to improve the fixation of hip joint prostheses including the femoral component thereof in the body so that the device implanted therein becomes as permanent as possible. Many orthopedic implants use a cement to anchor the stem portion of a femoral component in the femur. For example, United Kingdom Patent Specification No. 1,409,054 in the names of Robin S. M. Ling and Alan J. C. Lee discloses a hip joint prosthesis having a double-tapered stem which, among other advantages, enhances extrusion of cement caused by penetration of the stem during fixation. U.S. Pat. No. 3,793,650 discloses an intramedullary stem for a prosthetic bone joint device of this type also having a base with spring members intended to centralize the position of the stem in the canal or bore of the bone in order to insure a relatively uniform or, at least minimum thickness of cement between the wall of the bone and the stem. It has been found desirable to have a uniform mantle of at least two millimeters (2 mm) of cement between the stem and the bone.

The prior art has shown centralizers as a means for insuring that there will be at least a certain minimum thickness of cement between the stem of the prosthesis and the interior wall of the canal formed in the femur bone for receiving such stem, the likelihood of the stem protruding through the cement and contacting the interior of the femur bone itself is minimized. Thus, in those types of implants using cement, it is important to insure that the stem is completely encapsulated by the cement and does not protrude through to contact the bone.

One type of bone cement utilized to retain the stem of a femoral hip joint prosthesis in the canal of a bone comprises a mixture of polymethylmethacrylate (hereinafter PMMA) polymer and methyl methacrylate monomer and optionally including a styrene co-polymer of PMMA. This and other types of cement utilized for such purpose may be packaged in two separate components which are mixed into a paste which is placed in the canal of the femur immediately prior to insertion of the stem of the prosthesis. Such paste then sets to a relatively rigid material providing excellent adherence to the interior wall of the bone.

In both the cemented and non-cemented types of devices used heretofore, problems have arisen, particularly after a number of years of implantation. It has been found that the cement utilized to retain the stem of the device in the canal of the femur bone is subject to a phenomenon known as creep. Thus, while the bone cement appears to be rigid when set, it is subject to minute amounts of movement over time. The amount of creep encountered with such cement following implantation is exaggerated by virtue of the fact that the body temperature controls the temperature of the implanted cement and prosthesis. Thus, PMMA and other types of bone cement at body temperature are subject to a greater degree of creep than bone cement maintained at room temperature of, say, 72° F. This may be readily observed by mounting a bar of PMMA so that its ends are supported and applying a fixed load at the center of the bar. Tests have shown that a bar so supported and subjected to a load of 5 pounds for eight hours at 98.6° F. will deflect to an extent 3.5 times greater than an identical bar supported and loaded in an identical manner for eight hours at 72° F.

Over a period of time, the phenomenon of creep may result in disruption of the micro-interlocking of the cement-implant interface. This may allow the prosthesis to loosen and cause unwanted movement. In addition, the femoral component could subside as the cement deformed over time.

In the early 1970's a polished femoral hip component was designed which was intended to subside as the bone cement deformed over time. This stem is shown in the aforementioned U.K. Patent 1,409,054 and sold under the trade name Exeter® hip by Howmedica Inc. With this design, the prosthesis is wedge-shaped and automatically relocks itself within the bone cement as subsidence occurs due to bone cement creep.

As discussed in U.S. Pat. No. 5,171,275, it is well known that polishing the Exeter® hip stem allows for less adhesion between the bone cement and the prosthesis to permit subsidence. It has now been unexpectedly found that coating a polished prosthesis with the coatings of the present invention further reduces the bond between the prosthesis and the bone cement.

Coatings such as diamond-like coatings are known and may be applied to metal by processes described in U.S. Pat. Nos. 4,382,100, 4,394,400 and 4,645,977, the teachings of which are incorporated herein by references. The diamond-like films produced by these methods on a metal substrate are known to reduce friction (see U.S. Pat. No. 4,525,417). The coating of metallic orthopedic implants has been broadly taught in EPO publication 0 302 717 A1 and Japanese Patent Application 59-82851 (1984) but these publications did not address the advantages of using such a coating on a polished hip stem of the type disclosed in U.K. 1,409,054 designed to subside as bone cement creeps.

SUMMARY OF THE INVENTION

The present invention provides for a femoral hip joint prosthesis having a design which allows for subsidence of the stem within the cement mantle by reducing the bond between the prosthesis and the bone cement.

Accordingly, it is an object of the present invention to provide a new and novel femoral hip joint prosthesis which is specifically designed to markedly reduce the bond between the prosthesis and the bone cement by coating the prosthesis with an adhesive reducing composition.

It is a further object of the present invention to provide a femoral hip joint prosthesis which will not loosen but rather will self-tighten, even though the cement mantle creeps or expands fractionally over a period of time.

It is yet another object of the present invention to provide a femoral hip joint prosthesis in which the stem subsides within the cement as the cement creeps and thus is permitted to remain at all times in snug interfacial contact therewith, imparting in the stem area the reliable compressive forces against the cement which is micro-interlocked with the bony surfaces.

Finally, it is an object of the present invention to provide a femoral hip joint prosthesis in combination with a cement mantle implanted in the canal of a femur wherein said cement mantle encapsulates the stem of such prosthesis in an interfacial relationship which permits subsidence of the stem within the cement mantle without disrupting the interfacial adherence between the cement mantle and the bone.

The femoral hip joint prosthesis of the present invention is collarless, has a double tapered stem formed in the preferred embodiment, and has the surface of the stem highly polished to provide an extremely smooth surface. The stem is coated with a coating, for example, a layer of diamond-like carbon. It has been discovered unexpectedly that these coatings like Diamond-Like-Carbon (DLC) produce a highly abrasion resistant surface that has minimal adhesion to bone cement. This was an unexpected result, as many epoxy cements (other than PMMA) adhere quite readily to abrasion resistant coatings like DLC. Thus the application of DLC to the surface of a polished hip stem should result in increased fatigue strength, increased abrasion resistance, reduced adherence, and less bone cement debris. The lower end of the stem may be positioned in a hollow centralizer which serves to stabilize it and insures that an adequate thickness of cement encapsulates the stem. Such design permits the stem portion of the prosthesis to move fractionally within the cement mantle without disrupting the cement-bone interface and to self-tighten as the male component, namely, the distal tip of the stem engages further in the hollow centralizer.

The prior art's highly polished, tapered shape results in a low adhesion between the prosthesis and the PMMA bone cement. As a result of this reduced adhesion, bone cement debris generated by motion at the metal-cement interface are reduced. When adhesion is reduced even further, then wear debris are minimized. In addition, resistance to subsidence is reduced.

Although prior art prostheses such as the tapered collarless bone joint devices disclosed in the previously referenced United Kingdom Patent Specification No. 1,409,054 and U.S. Pat. No. 3,793,650 have been used with polished surface, they have never utilized an outer layer of, for example, diamond-like carbon to further reduce the bone between the prosthesis and the bone cement. The prosthesis of the present invention provides superior results over the prior art in that, as well as allowing enhanced subsidence within the cement mantle, it exhibits good corrosion resistance when implanted in the body. Furthermore, the coatings taught herein have a surface roughness which mimics that of the underlying polished surface.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 is a front elevational view of the femoral hip joint prosthesis, according to the present invention;

FIG. 2 is an end view of such femoral hip joint prosthesis;

FIG. 3 is a sectional view taken through line 3—3 of FIG. 1;

FIG. 4 is a sectional view taken through line 4—4 of FIG. 1;

DESCRIPTION OF THE PREFERRED EMBODIMENT

Figure 5:
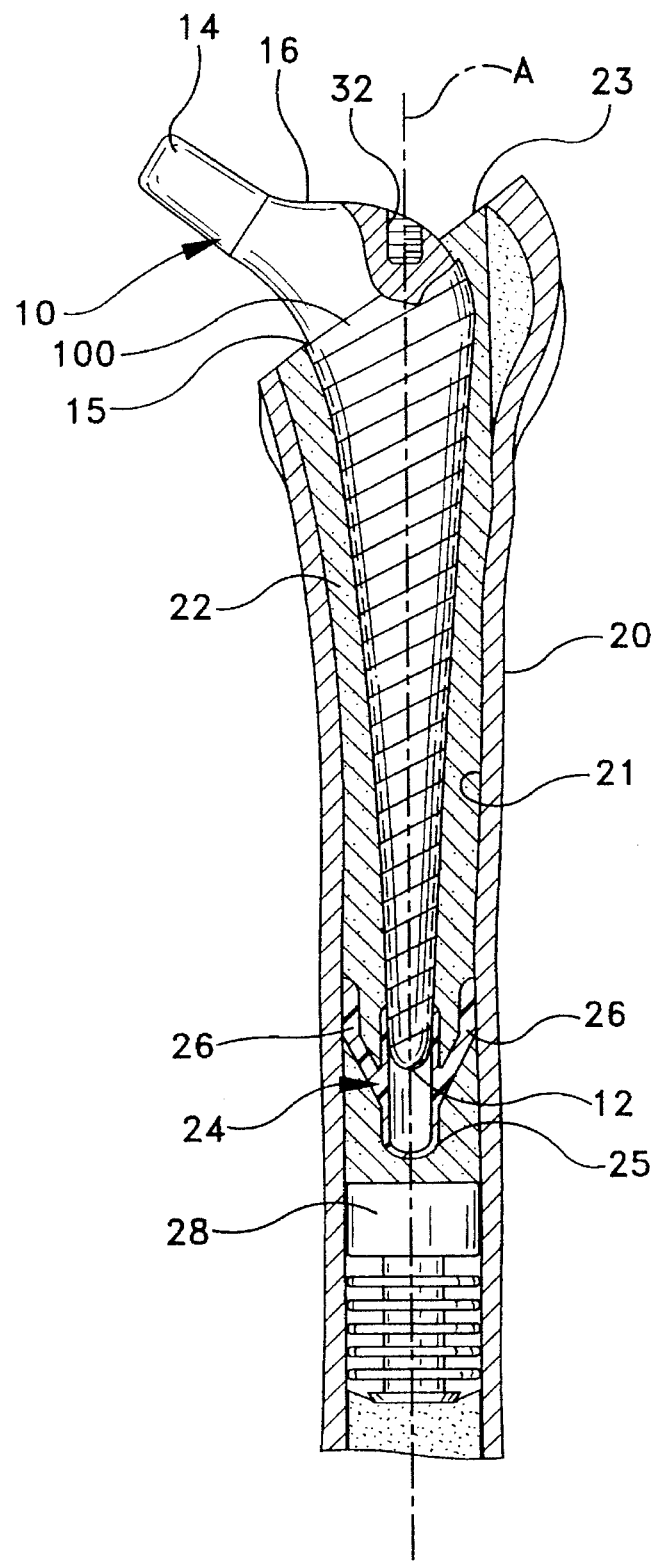
FIG. 5 is a sectional view showing the femoral hip joint prosthesis of the present invention immediately after implanting in a patient.

Referring now to FIGS. 1 and 2, there is shown a femoral hip joint prosthesis 10 having a stem 11 which is convergently tapered toward a distal end 12 and extending along a first axis of symmetry A to an area of juncture with a neck portion 13 lying on a second axis of symmetry B. The stem, in the area to be in contact with the bone cement, is polished, preferably to an average roughness of less than about 4 microinches and then is coated with a layer 100 of adhesion reducing coating, for example, diamond-like carbon coating at least 100Å thick and preferably about 1 to 3 microns. This coating may be applied by any well known method such as that disclosed in U.S. Pat. No. 4,382,100 and is preferably uniform and non-porous.

For example, a method of applying a carbonaceous material to a prosthesis surface may consist of placing the surface in an enclosure containing a gas at less than atmospheric pressure, the gas consisting substantially of carbon and hydrogen; and simultaneously generating a plasma in the gas in said enclosure and applying to the surface through capacitive means an electrical potential which changes sign at time intervals of between $5\times10^{-9}$ and $10^{-6}$ seconds.

The surfaces of the prostheses may be of conducting or semiconducting material, when the capacitive means Comprises a separate capacitor, or the surfaces may be of an insulating material, when the bodies of material may themselves comprise the capacitive means.

The gas will normally be a hydrocarbon compound with the optional addition of a small proportion of another gas if a "doped" carbonaceous layer is required on the surface.

The plasma may be generated in a two electrode system by a source of radio frequency or may be generated in a three electrode system by separate means, for example an additional radio frequency source or a hot cathode or a cold cathode glow discharge arrangement.

In a two-electrode system, the plasma is generated by connecting the prosthesis surface through capacitive means to one terminal of a source of electromagnetic radiation at a frequency of between 0.5 and 100 megahertz, and connecting the other terminal of the source to an electrode spaced from the surface.

The preferred prosthesis 10 further includes a neck portion 13 which is a frustoconically shaped Morse taper neck 14 to which may be attached a spherically shaped Morse taper head. As is clear from FIG. 1, no collar is provided in the femoral hip prosthesis, but rather the portion of the prosthesis joining the stem 11 to the neck 13 follows a smooth arcuate contour in the area 15 of the included angle between the respective axes of symmetry A and B. The portion of the femoral hip prosthesis 10 opposite the smooth arcuate portion 15, namely, that portion on the outside of the angle between the two axes of symmetry A and B, has an enlarged shoulder 16.

Preferably, an aperture 18 may be provided in the area of the neck and shoulder to assist in removing the prosthesis 10 in the event revision is required at some future time.

As can be seen in FIGS. 3 and 4, the stem 11 is tapered in both directions and preferably has rounded corners 19. As pointed out in United Kingdom Patent Specification 1,409, 054, such double tapering enhances the extrusion of cement caused by penetration of the stem 11 thereinto during fixation. The coating 100 as shown in FIG. 4 is greatly exaggerated in thickness for illustration purposes.

The femoral hip joint prosthesis 10 of the present invention may be formed of high strength forged Co—CR—Mo alloy (ASTM designation F-799) and has its surface polished to a high degree (also known as a buff finish) to provide for a smoothness having a target surface roughness preferably of about four (4) microinches. Of course, stainless steel or other biocompatible materials, even composites, can be used to make the stem base material. The coated polished Vitallium® Co—Cr—Mo alloy or stainless steel stem is superior to metal alone because the coating better resists pitting and crevice corrosion of the metal in the body environment as well as reducing the bone strength between the bone cement and the prosthesis.

It is the combination of the Co—CR—Mo alloy having its surface and polished and coated with, for example, diamond-like carbon coupled with the tapered stem and collarless design which permits the tapered stem and collarless design which permits the femoral hip prosthesis of the present invention to function in the manner intended without loosening and without causing pain or other adverse mechanical effects in the patient even though there is subsidence of the prosthesis over a period of time. Thus, the present design permits the polished and coated stem to subside within the cement mantle. The taper of the stem permits it to self-tighten upon the slight movement which occurs during the subsidence and engage in the hollow centralizer and yet to do so without pulling the cement mantle and thus avoid disrupting the micro-interlocking at the cement-bone interface. Such design causes the stem to impart primarily compressive forces against the cement mantel, thus transmitting the load to the femur. Transmitting the load in this manner forces the cement mantle continuously snugly and firmly against the interior of the femur to assist in maintaining the integrity of the micro-interlocking at the cement-bone interface.

EXAMPLE

In order to test the effect of diamond-like Coatings on a cobalt chrome stem, diamond-like carbon coatings were applied to highly polished (less than about 4 microinches) Vitallium® (CoCr) discs by Diamonex Inc., of Allentown, Pa. as a commercial service, using diamond-like carbon deposition technology similar to that discussed above. These coatings were greater than 100Å preferably and up to several microns for improved wear purposes. The maximum thickness of the coatings is not material to the reduction of bond strength between the prosthesis and the bone cement as long as the surface finish is maintained. Uncoated, highly polished Vitallium discs were used as controls. All the discs were ultrasonically cleaned in methanol and dried. Size 0.7134 cm diameter aluminum "pull studs" having a flat bottom surface were abraded with 180 grit and sand paper, washed with methanol, and dried.

The Howmedica Simplex P® bone cement was mixed per manufacturers instructions using a Howmedica Simplex® enhancement mixer. Sufficient mixed cement was placed on the flat portion of the pull stud to permit complete coverage of the pull studs face when pressed against the test specimens. The cement coated pull stud was pressed against the surface of the polished test specimens and held in place with a metal clip until the cement cured completely, approximately two hours.

The pull stud with the attached test specimen was placed in a Sebastian Five-A materials tester and fixed in the tester's holder as per manufacturers instructions. The pull rate was set for 28.57 Kg/min. After completion of the test cycle, the force required to pull off the test specimen was recorded. The testing equipment output was convened to adhesive strength by dividing the displayed pull off force (in Kilograms) by the attachment area of the pull stud (in square centimeters) to yield a value in units of $Kg/cm^2$.

The following table shows the adhesive strength of both diamond-like carbon coated polished Vitallium® cobalt chrome and untreated polished Vitallium® control discs. In addition, other coatings such as Chromium carbide, Chromium nitride, Titanium nitride, Titanium carbon nitride, Chrome and Zirconium were used to coat a polished Vitallium® hip stem. These coatings were also greater than 100Å and up to about 3 microns.

TABLE

TENSILE ADHESION VALUES OF PMMA BONE CEMENT TO VARIOUS COATED VITALLIUM SUBSTRA

| DLC Coated Vitallium | All values are in $Kg/cm^2$ | |
|---|---|---|
| Sample 1 | 18.7 | |
| 2 | 7.2 | |
| 3 | 5.7 | |
| 4 | 20.0 | |
| 5 | 15.0 | |
| 6 | 13.6 | |
| 7 | 12.4 | |
| Average of 7 samples | 13.23 | |
| Coated Vitallium (non-DLC) | Average Values $Kg/cm^2$ | Commercially Available From: |
| Chromium Carbide * | 2.8 | *Richter Precision, East Petersburg, PA |
| Chromium Nitride ** | 0 | **Balzers, Mt. Clement, MI |
| Titanium Nitride *** | 38.1 | ***Richter Precision and Balzers |
| Titanium Carbo-Nitride ** | 18.1 | |
| Amorphous Metallic Chromium **** | 49.7 | ****Electrolyzing Inc., Providence, RI |
| Zirconium, Ion Implanted ***** | 54.2 | *****Implant Sciences Inc., Wakefield, MA |
| Uncoated Vitallium Controls | | |
| Sample 1 | 60.0 | |
| 2 | 56.0 | |
| 3 | 40.4 | |
| 4 | 101.8 | |
| 5 | 87.8 | |
| 6 | 99.1 | |
| 7 | 96.8 | |
| 8 | 82.1 | |
| 9 | 95.6 | |
| 10 | 117.6 | |
| 11 | 117.3 | |
| 12 | 100.1 | |
| 13 | 99.4 | |
| Average of 13 Samples | 88.8 | |

The interface adhesive strength between the Vitallium with the diamond-like coatings and the Simplex P® bone cement was unexpectedly almost four times less than the interface strength between Simplex bone cement and uncoated Vitallium® control samples.

The table also shows the adhesive strength of the other coatings (all applied commercially at the locations listed) at thicknesses of greater than 100Å and preferably 1 to 3 microns and more preferably 1 micron, which also reduce the bond strength of the bone cement to the Vitallium. All were less than the Vitallium control adhesive strength of Table I.

Again, the bond or adhesive strength between these coatings on the Vitallium and the bone cement is less than that of the control sample. While highly polished Vitallium was used in the above tests, other polished metals such as stainless steel or composite materials can be coated and similar reductions in bone cement bond strength to the prosthesis can be expected.

Referring now to FIG. 5, there is shown the femoral hip joint prosthesis 10 of the present invention coated with, for example, diamond-like carbon immediately following its implantation in the femur bone 20. As is customary, the femur bone 20 is prepared by reaming a canal 21 into which PMMA such as Simplex P® from Howmedica Inc., or other suitable bone cement, is introduced under pressure. Promptly after introduction of the bone cement into the canal 21 and before the cement has had an opportunity to set, the stem 11 of the femoral hip joint prosthesis 10 is inserted into the cement with the result that a cement mantle 22 is formed around the stem 11 up to the arcuate area 15 and a portion of the enlarged shoulder 16. Any excess cement is wiped away leaving an exposed upper end 23. The free or distal end 12 of the stem 11 may be engaged in a hollow plastic centralizer 24 which insures that there will be a sufficient thickness of cement around all portions of the stem or a preformed sheath as shown in U.S. Pat. No. 5,197,990. The optional plastic centralizer 24 includes a cup-shaped pocket 25 having a plurality, preferably 3 or 4, of integrally formed resilient arms 26 sized to engage the interior of the canal 21. The hollow cup-shaped pocket 25 of the centralizer may be filled with a compressible material such as Avitin Powder, Surgicell, Gelfoam or the like such that there will be no interference with subsidence of the distal end 12 of the prosthesis 10 within the hollow pocket 25 of the centralizer. Prior to introduction of cement in the canal, a cement restrictor 28 may be positioned therein.

Figure 6:
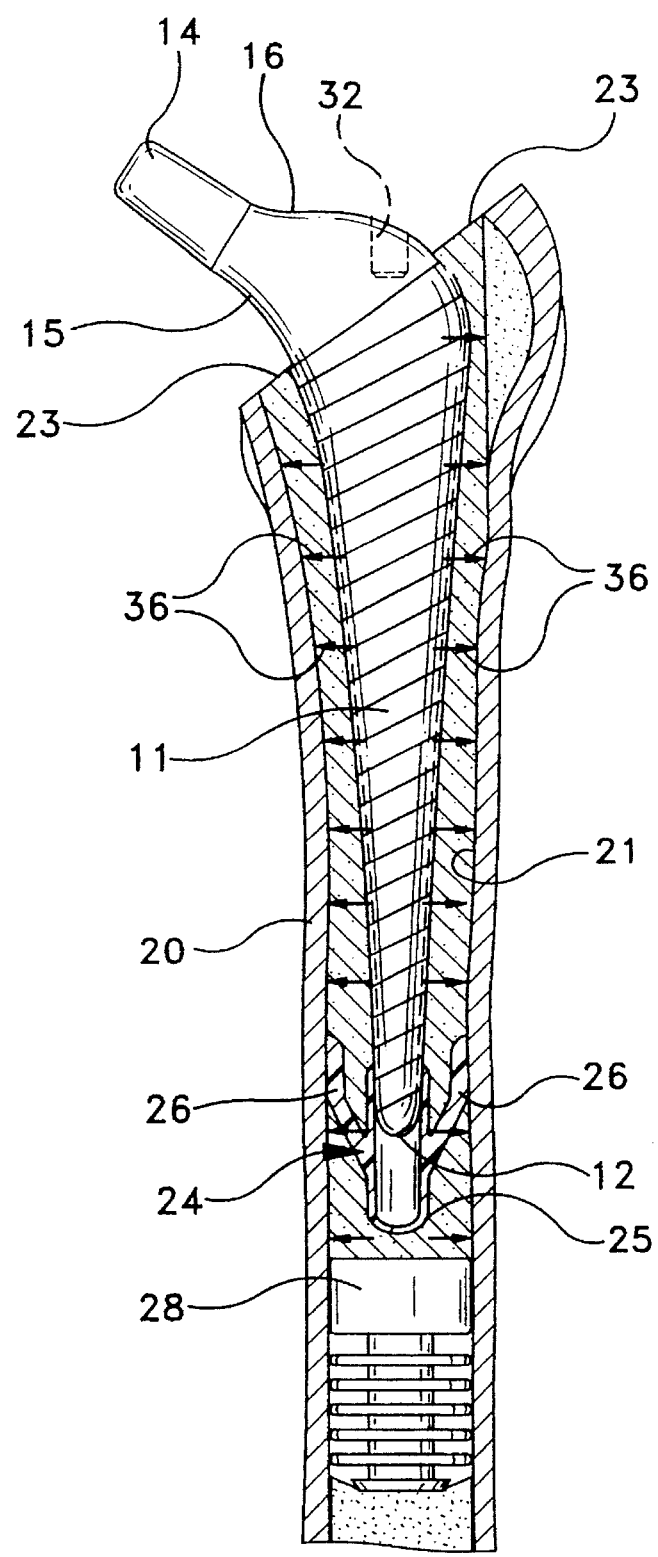
FIG. 6 is a view similar to FIG. 5 showing the femoral hip joint prosthesis after being implanted for a number of years and showing, greatly exaggerated, the effects of subsidence.

FIG. 6 shows the implanted femoral hip joint prosthesis 10 after an extended period, say ten years, following implantation. As can be seen, there has occurred a small amount of radiological subsidence, on the average of 2 mm, where the stem 11 has subsided within the cement mantle 22. As may be seen in FIG. 6, such subsidence within the cement mantle results in the distal end 21 moving further into the centralizer 24 and in the enlarged shoulder 16 pulling away from the cement mantle 22 leaving a gap 27. Because of the tapered stem, collarless design of Co—Cr—Mo alloy having a highly polished surface coated with diamond-like carbon or the other coatings set forth above, the femoral hip joint prosthesis 10 of the present invention is permitted to more easily subside within the cement mantle 22 end to do without disrupting the cement-bone interface. Thus, the subsidence of the stem 11 results in microscopic movement of the stem 11 in relation to the adjacent surface of the cement mantle 22. As will be appreciated and as shown schematically in FIG. 8, the effect of such microscopic movement is to cause the stem 11 to self-tighten as it and the cement mantle 22 subside and to impart primarily compressive forces against the cement mantle 22 in directions substantially normal to the interior surfaces of the bone 20. This is illustrated schematically by the arrows 36 in FIG. 6.

While several examples of the present invention have been described, it is obvious that many changes and modifications may be made thereunto, without departing from the spirit and scope of the invention.

We claim:

1. A method for implanting a femoral hip joint prosthesis having a reduced adhesion to bone cement in an intramedullary canal comprising the steps of:

providing a prosthesis having an elongated stem extending from a proximal end to a distal end, said stem tapering from a relatively larger cross-sectional size adjacent said proximal end to a smaller cross-sectional size adjacent said distal end and being formed of a biocompatible metal alloy and having substantially all surfaces with a polished finish with the polished surface being coated with a layer of diamond-like carbon to reduce adhesion to bone cement, said layer of material is from about 1 to 3 microns thick with an outer surface maintaining said polished surface roughness: and implanting said prosthesis in bone cement.

2. The femoral hip joint prosthesis of claim 1 wherein the polished surface has a roughness of less than about 4 microinches.

* * * * *